United States Patent [19]
Hersh et al.

[11] Patent Number: 5,829,449
[45] Date of Patent: Nov. 3, 1998

[54] SMOKING PRODUCTS CONTAINING ANTIOXIDANTS

[75] Inventors: Theodore Hersh; Rebecca Hersh, both of Atlanta, Ga.

[73] Assignee: Thione International, Inc., Atlanta, Ga.

[21] Appl. No.: 933,696

[22] Filed: Sep. 19, 1997

[51] Int. Cl.$^6$ .............................. A24D 1/04; A24B 3/18; A24B 15/00; A24B 15/10
[52] U.S. Cl. .................... 131/202; 131/298; 131/331; 131/334
[58] Field of Search .................... 131/202, 298, 131/331, 334

[56] References Cited

U.S. PATENT DOCUMENTS

| | | | |
|---|---|---|---|
| 4,520,134 | 5/1985 | Rosen | 514/625 |
| 5,060,672 | 10/1991 | Irimi et al. | 131/331 |
| 5,364,617 | 11/1994 | Bush et al. | 424/59 |
| 5,403,834 | 4/1995 | Malfroy-Camine et al. | 514/185 |
| 5,462,963 | 10/1995 | Bush et al. | 514/248 |
| 5,780,489 | 7/1998 | Brooks | 514/369 |

Primary Examiner—Stanley S. Silverman
Assistant Examiner—Jacqueline A. Ruller
Attorney, Agent, or Firm—Malcolm B. Wittenberg

[57] ABSTRACT

A composition for inclusion within a cigarette, cigar or pipe. The composition can be included within the tobacco itself, a filter for filtering tobacco smoke once burned or even within the paper or wrapper surrounding the tobacco product. The composition is capable of reducing free radical damage to the oro-pharyngeal cavity, respiratory tract and lungs resulting from tobacco smoke. The composition includes L-glutathione and a source of selenium such as selenomethionine.

47 Claims, No Drawings

SMOKING PRODUCTS CONTAINING ANTIOXIDANTS

TECHNICAL FIELD OF THE INVENTION

The present invention deals with the combination of various synergistic antioxidants, enzymatic co-factors and amino acids in appropriate delivery vehicles employed in cigarette filters and in external filters such as cigarette and cigar "holders," in "pipe filters" and in tobacco, wrappers and papers as a means of preventing or ameliorating signs and symptoms and complications to the oro-pharyngeal cavity, respiratory tract and lungs from damage by tobacco smoke induced free radical species from filter cigarettes or from tobacco smoke from unfiltered cigarettes, cigars or pipes.

BACKGROUND OF THE INVENTION

The deleterious effects of tobacco abuse are well known and regulatory agencies as well as the public constantly react to these scientific and epidemiologic evidences. Tobacco is indeed a worldwide public health hazard accounting for significant morbidity and mortality. Although smoking places an abundant oxidant insult to the oral cavity respiratory tract and lungs, evidence supports the notion that the oxidant burden is on the entire organism of the smoker. Smoking promotes development or enhancement of atherosclerosis, causing cardiovascular disease, chronic obstructive pulmonary disease, recently labeled "smoker's lung," cutaneous damage, especially to the face, called "smoker's face," and various forms of cancer, including carcinomas of the mouth, pharynx, esophagus and lung.

Tobacco is a substance consisting of the dried leaves and stems of the plant *Nicotiana tabacum*. Tobacco contains the drug nicotine, which is very addictive. The plant is native to North America and now is grown worldwide. Tobacco abuse has been identified as the single most preventable cause of disease, morbidity and mortality, for tobacco smoke contains many toxic chemicals, in tar and gas phase smoke.

There are three principal ways to consume tobacco: 1) smoking, 2) chewing and dipping, and 3) snuffing. Fifty million Americans smoke, and countless others are affected by tobacco smoke, the so called secondary or environmental smokers. Children of smokers also breathe this second-hand smoke and have more respiratory problems than children of non-smokers. Smokeless tobacco is used by as many as 12 million individuals and has detrimental effects on the oral cavity plus systemic effects derived from buccal absorption of nicotine and other chemicals.

Cigarette smoke is divided into two phases, tar and gas-phase smoke. Cigarette tar contains high concentrations of free radicals. Common oxidants include semiquinone which is in equilibrium with hydroquinones and quinones, particularly in the viscous tar matrix. Many tar extracts and oxidants, including the latter mentioned, are water soluble and reduce oxygen to its superoxide radical which can dismutate to form $H_2O_2$. Importantly, glass-fiber type cigarette filters retain almost all of the tar particles that are larger than 0.1 micron. Thus, the filter acts as a trap for tars in cigarette smoke. There are an inordinately large number of free radicals, greater than $10^{15}$, in each puff in the gas-phase of cigarette smoke. While oxidants in tar are stable, those organic radicals in gas phase smoke are reactive carbon and oxygen centered radicals with extremely short half lives. Other free radical species, such as the aldehyde species have longer half-lives and may be more deleterious, resulting from lipid peroxidation. Interestingly, concentrations of free radicals from tobacco are maintained at high levels for more than 10 minutes and tend to increase as tobacco smoke is aged. It is thus considered that these gas phase smoke oxidants are in a steady state as they are both continuously formed and destroyed. The latter reactions are similar to those noted to occur in smog, pointing to the extra noxious stimuli to primary and secondary smokers in atmospheric polluted environments.

In other in vitro studies, gas-phase cigarette smoke was assessed in its filtered and whole (unfiltered) states for oxidative effects on human plasma. Investigators noted the prevalence of lipid peroxidation in plasma after exposure to gas phase smoke, but not to whole cigarette smoke. The reaction of lipid peroxidation did not commence until the endogenous ascorbic acid had been consumed, that is, vitamin C was oxidized completely. They also noted that cigarette smoke exposure caused oxidation of plasma protein thiols (methionine and cysteine amino acid linkages) and low density lipo-proteins. They concluded that lipid peroxidation induced by the oxidants of gas-phase smoke leads to changes in lipoproteins associated with atherogenesis. As noted herein, the synergistic effect of reduced glutathione and ascorbic acid or ascorbic acid derivatives such as their esters, are beneficial to combating tobacco oxidants in both ameliorating and delaying the untoward effects of tobacco smoke on oral, pharyngeal and respiratory epithelia, on bronchoalveolar fluids and on lung parenchyma.

Cells subjected to oxidative stress may severely affect cellular function and cause damage to membrane lipids, to proteins, to cytoskeletal structures and to DNA. Free radical damage to DNA has been measured as formation of single-strand breaks, double-strand breaks and chromosomal aberrations. Cells exposed to ionizing radiation and cigarette smoke have also been demonstrated to have an increased intracellular DNA damage, hence the frequency of oro-pharyngeal, esophageal, and pulmonary carcinomas in tobacco users.

Macrophage cells and neutrophils have their phagocytic activity associated with the so-called "respiratory burst" reaction, which is dependent on the plasma membrane NADPH oxidase. The oxygen radical may then be transformed to $H_2O_2$ by superoxide dismutase. Clausen [full citation] showed that smokers have a higher respiratory burst reaction of alveolar macrophages and peripheral neutrophils than non-smokers and the former also have higher incidence of oral and respiratory signs and symptoms than non-smokers, due to their exposure to inspired particles. The "respiratory burst" reaction may also destroy elastic fibers due to neutrophile's secretion of elastase and may also damage alpha-1 anti-trypsin. It was shown that a decrease of the affect of the "respiratory burst" reaction in smokers supplemented with oral mega doses of antioxidants occurred. The affects on the latter were evaluated with vitamins E and C, and beta-carotene in 10 smokers and 10 controls.

Other investigative studies have shown that tobacco smoke impairs alveolar machrophages' phagocytic function. Tobacco gas-phase from unfiltered cigarettes is a potent inhibitor of their G-3P-dehydrogenase enzyme, accounting for phagocytic dysfunction, probably through blocking of enzyme-sulfhydryl groups since protection is generally afforded by the sulphur amino acid cysteine. Evans and co-workers (arch environ hlth: 103–106, 1979) [full citation] studied the affects of four types of cigarette filters on the inhibition of this enzyme by aqueous solutions of free gas-phase tobacco smoke. They concluded that hydrogen sulfide was the main inhibitor in this smoke and inhibition was dependent on age and amount of the free gas-phase solution, as well as contact time. Commercial cellulose acetate-charcoal filters were effective in removing this inhibitor. Green [full citation] has also shown the protective role on alveolar macrophages from cigarette smoke by both reduced glutathione and by L-cysteine. Both these antioxidants are sources of protective sulfhydryl groups.

The lungs have adapted biochemical enzymatic and non-enzymatic antioxidant systems as prevention, limitation or reversal of oxidant damage to the lungs. This is a protective feature to maintain normal, pulmonary function, as the respiratory tissues operate in an environment of high partial pressure of oxygen and are continuously exposed to airborne pollutants. Because of their access to the environment, like the skin to oxygen and ultraviolet radiation, the lungs may be damaged by inhaled gaseous and particulate matter, particularly in both active and passive smokers. Lung injury may produce alterations in the tone of both the pulmonary and tracheobronchial circulations resulting in plasma exudation. Locally, airway edema may narrow airway lumen or fluid may accumulate in alveolar spaces, such as occurs in adult respiratory distress syndrome (ARDS).

Bronchial hyperactivity, as in asthma, may also result from these cytological injuries, ultimately culminating in reduction of pulmonary function, as evidenced by blood oxygen desaturation and local accumulation of carbon dioxide. This is the so-called "smoker's lung".

Reactive oxidizing species, as induced by inhaled tobacco, smoke, ozone smog and others are important factors in bronchial hyperresponsiveness and inflammatory lung injury. As in other tissues, antioxidant enzymes in the lung include superoxide dismutase (SOD), which converts superoxide to hydrogen peroxide and catalase which reduces hydrogen peroxide to water. This reaction may also be catalyzed by selenium cofactor enzyme glutathione peroxidase using reduced glutathione (GSH) as a substrate. Glutathione peroxidase may also reduce lipid peroxide to the corresponding alcohols also using reduced glutathione.

The ubiquitous non-enzymatic thiol tripeptide, glutathione (GSH), plays a vital function in maintaining the integrity of the reactive oxygen species-free radical sensitive cellular components. This is accomplished through its direct role as an antioxidant, in its reduced (GSH) form, as well as a cofactor, as aforementioned. GSH has been detected in bronchoalveolar lavage fluid. In cells, GSH is oxidized in this process to GSSG, but its cellular concentrations for antioxidant activity is maintained in equilibrium by the enzyme glutathione reductase, consuming NADPH as the source of reducing equivalents. Under states of GSH depletion, including malnutrition and severe oxidative stress, as in smoking, cells may become injured and die.

Other non-enzymatic molecules playing an antioxidant role in the lung include the ascorbates (vitamin C); particularly in the extracellular defenses of the lung, as teleologically, it is present in high concentrations in the pulmonary airway lining fluid. Ascorbates as free radical scavengers also react with oxidized glutathione (GSSG) to reduce it to GSH. Also, in the lipid-membrane of the cells, the hydrophobic alpha-tocopherols (vitamin E), acts synergistically with vitamin C to inhibit lipid peroxidation, as may be induced by cigarette smoke, by actively scavenging lipid peroxides and other free radicals.

Various studies have correlated the importance of oxidant stress to various organs resulting from tobacco smoke and other noxious environmental factors and thus continue to exert a toll on the public health of all countries. Significant morbidity and mortality result from smoking tobacco from cigarettes, cigars, and pipes and local oral pathology from both smoking and chewing tobacco. Epidemiologic studies have strongly implicated tobacco in the pathogenesis of atherosclerosis and coronary artery disease, emphysema and various malignancies, including oro-pharyngeal and pulmonary neoplasias. Chronic cigarette smoking is associated with appearance of free radicals inducing oxidative damage. Measurement in blood, urine and tissues of various antioxidants or of by-products of free radical metabolic processes are supportive of tissue oxidant damage in the pathogenesis of various diseases associated with tobacco smoking and environmental pollutants. An example to be cited is one of the F2 isoprostanes, 8-EPI-prostaglandin 2a, a stable product of lipid peroxidation, which may be assayed by chromatography in plasma or urine. Chronic smokers, particularly "heavy" smokers, have higher urinary levels of 8-EPI-PGF 2a, than matched, non-smoker control subjects. Cessation of smoking with or without switching to nicotine patches, reduced the urinary levels but not to the normal ranges. Further studies, while subjects continued to smoke, revealed that oral administration of ascorbic A-acid (vitamin C) with its known antioxidant properties reduced urinary 8-EPI-PGF 2a levels, suggesting in vivo suppression of oxidant damage in the body.

Studies have estimated that tobacco smoke has over 3,000 different constituents, of which a number are toxic, some are carcinogenic and many generate free radical species. Most of these compounds have been identified in so-called mainstream and sidestream tobacco smoke. The former is that volume of smoke drawn through the mouthpiece of the tobacco product during puffing while sidestream smoke is that smoke emitted from the smoldering cigarette in between puffs. Although tar and nicotine are retained in the filter of cigarettes, this applies mainly to mainstream smoke, when comparing filter and non-filter cigarettes. Mainstream smoke emission is also markedly reduced both in low and in ultra low yield cigarettes. However, the emissions of toxic and carcinogenic components in sidestream smoke are not significantly reduced in filter cigarettes when compared to their non-filter counterparts. Thus, sidestream smoke is a major contributor to environmental smoke, affecting both the smoker and their non-smoking counterparts, so called secondary smokers. The lower rates of consumption of cigarettes with high smoke yields has not reduced the indoor pollutants of carcinogenic substances and free radicals generating potential of tobacco smoke produced in sidestream smoke, albeit their diminished levels in mainstream smoke by smoking low yield tobaccos and filter cigarettes.

Tobacco, whether smoked as cigarettes, cigars or pipe causes common untoward effects in the oral cavity. Tobacco smoke has two chances to exert its deleterious effects in the mouth: when it is inhaled by the smoker and on its exit during exhalation.

Leukoplakia, a tobacco induced white patch on the buccal mucosa, as found in smokers, is a localized irritation due to direct contact of smoked tobacco and it is directly related to the frequency and years of tobacco abuse. Although leukoplakia is a benign oral lesion, these have a malignant potential, requiring a biopsy of the lesion to rule out cancer. Leukoplakia may regress or resolve completely when use of tobacco products is discontinued.

Over 30,000 new cases of cancer of the oral cavity are diagnosed annually, accounting for two to four percent of all new cancers. Oral cancer kills 8,000 patients each year and only half of cases diagnosed annually have a five year survival. The great majority of these patients are users of tobacco products. Other risk factors include alcohol abuse, nutritional deficiencies and poor oral hygiene.

Tobacco contributes to other oral symptoms or pathologies of the mouth and teeth. Tobacco may cause halitosis, may numb the taste buds, interfere with the smell and the taste of food and may stain teeth and contribute to dental caries. For example, smokers have more dental tartar (calculus) than non-smokers. Tobacco is also associated with destructive periodontal (gum) disease and tooth loss. Acute necrotizing ulcerative gingivitis ("trench mouth") is a destructive, painful inflammatory condition occurring mainly in cigarette smokers. Swelling of the nasal and sinus membranes have also been associated, purportedly, in individuals who are "allergic" to tobacco smoke.

Like cigarettes, evidence shows that cigars are also toxic and addictive. Cigar and cigarette smokers have a similar increased risk for oral and laryngeal cancers but the latter smokers are more prone to contract cancer of the lung, emphysema and cardiovascular disease. While cigarette tobacco is generally flue cured with a resulting mildly acidic product, the slower curing methods for cigars render these mildly alkaline. At this pH, nicotine is more readily absorbed. Unlike cigarettes, cigars are less homogenous and vary in size and nicotine content. Cigar smokers may spend an hour smoking a single large "Havana" although some actively inhale very little of this smoke; however, in non-inhalers, their nicotine levels may be elevated with no toxic co-absorption, as occurs in cigarette smokers. Cigar smokers also commonly hold an unlit cigar in the mouth, exposing the oral cavity to further nicotine by local absorption. Thus, consumption of cigars may produce an equal or greater smoke burden of exposure and locally generated free radicals in the oral cavity which create deleterious effects and a risk of oro-pharyngeal cancer.

Carcinoma of the lung and chronic lung disease have been known to be end stage complications of cigarette abuse. Nicotine tars contain carcinogens and smoking induces also a free radical reaction in the respiratory tract, both putative to the oro-pharyngeal and pulmonary diseases and neoplasias induced by tobacco abuse. Cigarette filters "trap" nicotine tars but not the gas-phase compounds. Epidemiologic studies have been done in various countries to show the differential effects of tar content, amount of cigarettes smoked, type of tobacco smoked, and use of filters on oro-pharyngeal and lung cancer risk in cigarette smokers. The effect of smoking cessation on these respiratory diseases has also been investigated.

Under the epithelial lining along the respiratory airways there is a rich network of micro vessels which carry systemic blood from the nasal and tracheobronchial arteries. These vessels provide nutrition to the mucosa to enable it to maintain the protective functions. Vascular leakage of proteinaceous plasma is a cardinal sign of pulmonary inflammation, whatever the source of the stimulus, including tobacco smoke. Because of differential in hydrostatic pressures, this exudation of plasma is a unidirectional outward movement, which becomes a specific defense and inflammatory response. This exudation thus results from a variety of inhaled provocations including noxious chemicals, gases, particulate matter, and bacteria, to the airways' mucosa. This first line of defense initially is non-injurious and reversible, but overwhelming or chronic and persistent stimuli, as tobacco smoke and other environmental pollutants, may cause pulmonary damage from the oxidative damage of the leucocytes, other free radicals and noxious agents.

As already noted, cigarette smoking may result in the sign-symptom complex known as chronic obstructive lung disease culminating in emphysema. Some clinical observations on the untoward effects of smoking are derived from an inherited multi-organ disease called alpha-1-antitrypsin deficiency. This inherited homozygous alpha-1 protease inhibitor deficiency, results in emphysema, but occurs in those patients who smoke at an earlier age, than in the tobacco smoking population without this inherited defect. Smoking results in impaired local protease inhibitors which function to protect pulmonary elastin tissue.

In patients with acute onset or flare-ups of bronchial or pulmonary diseases, inflamed respiratory epithelium and pleural exudates occur consequent to accumulation locally of leucocytes in response to the specific etiologic agent or responsible pathogens in infectious disease (tracheobronchial or pulmonary). White blood cells' function is to combat the deleterious agents or putative microorganisms, which cause the release of hydrogen peroxide and various enzymes, including myeloperoxidases, into extra-cellular fluids. These myeloperoxidases are able to catalyze hydrogen peroxide in the presence of chloride ion forming the strongly reactive species hypochlorous acid. HOCl then oxidizes tissue components and plasma protease inhibitors.

The lungs are very susceptible to damage caused by inhaled noxious agents rendering a response to this injury by respiratory epithelial cells and pulmonary vascular endothelium. Bacteria, fungi and viruses may also induce pulmonary infections. All aforementioned evoke respiratory tissue free radical reactions and antioxidant-inflammatory responses. Teleologically, as a front line defense mechanism to inhaled particles and gases, the respiratory tract and lungs count on active enzymatic and non-enzymatic antioxidants defense mechanisms to prevent, minimize, reverse and even repair this oxidant damage to the respiratory tract and lungs. The former includes superoxide dismutase, which converts deleterious superoxide radical to hydrogen peroxide and catalase which reduces $H_2O_2$ to water. This latter reaction may also be catalyzed by selenium containing glutathione peroxidase which may also reduce lipid hydroperoxides, products of oxidant induced lipid peroxidation, to alcohols, also using glutathione as the source of reducing radicals. Thus, the thiol tripeptide, glutathione, (GSH) acts as a direct antioxidant and as a cofactor in reactive oxygen species defense mechanisms. In this process, glutathione becomes oxidized but its cellular concentration as a reduced compound is maintained by the related enzyme glutathione reductase.

It is noted as well that some cells have sodium dependent up-take systems for GSH, allowing cells to use both exogenous GSH and endogenously synthesized GSH, thereby enhancing a cell's ability to survive oxidative and free radical species damaged in this fashion, extra-cellular GSH also protects cells' survival. Investigative studies have shown that cells' viability correlates best with content of GSH in mitochondria. In the absence of GSH, lipid peroxidation is uncontrolled and leads to cell injury and death. Conversely, GSH protects cells from the ravages of free radicals, working synergistically with the antioxidant enzymes and the dietary vitamin antioxidants.

Non-enzymatic antioxidants also protect the lungs from damage resulting from an oxidant favoring environment. Ascorbates (Vitamin C) are free radical scavengers in pulmonary extra cellular tissue and surface fluids and interact with oxidized glutathione synergistically to return glutathione it to its metabolically active form as a reduced molecule.

Vitamin C, ascorbic acid, plays a major role in human metabolism. As an antioxidant, it protects the skin from free radical damage induced by radiation, tobacco smoke, and other inhaled or swallowed environmental pollutants. Vitamin C promotes collagen synthesis, tissue repair and wound healing. Vitamin also renders important protection against damaging chemicals associated with cigarette smoking, including nicotine, carbon monoxide, n-nitrous compounds, nitrogen oxides, nitric acid gas and others. Although ascorbic acid may be reduced in this scavenging role, the ascorbate radical may then be removed by the NADPH enzyme systems as sources of reducing molecules. Thus Vitamin C may be recycled to abate or lessen the process of lipid peroxidation by its synergistic function with the tocopherols. Markham's patent (U.S. Pat. No. 4,822,8916) refers to the oral administration of Vitamin C to demonstrate its free radical attributes.

Cigarette smokers often have lower plasma levels of ascorbic acid than matched non-smoking controls. Clinical and investigative evidence suggests that smokers may have higher ascorbic acid requirements and that supplementing dietary vitamin C may be protective to the smoker.

Vitamin A is an essential nutrient to humans. Relative vitamin A deficiency may adversely affect the skin and mucous membranes, including the mucosa of the oral cavity and respiratory tract. These alterations are reversible on oral repletion with vitamin A or one of its many derivatives, all commercially available. Retinol is the transport form of vitamin A in plasma, while retinol ester is its storage form in the liver and in mucous membranes. Mucosal vitamin A deficiency has been reported in patients with bronchitis, after nicotine inhalation, and with premalignant mucosal lesions. Biesalski, in U.S. Pat. No. 5,112,598, dated May 12, 1992, described the use of vitamin A compounds so that these may be transported by the specific molecule retinol binding protein, and thereby correct that vitamin deficiency without creating toxic levels. The '598 patent, which is herein incorporated by reference, proposed pharmaceutical preparations of retinoid acid or its esters or esters of retinol as the active substance. For the respiratory tract in particular, aerosol preparations for topical use were proposed and described.

Waterbury in U.S. Pat. No. 3,667,478, dated Jun. 6, 1972, which is herein incorporated by reference, disclosed a filter cigarette incorporating a stabilized form of an aqueous emulsion of an active vitamin A preparation. This patent teaches that the method provides stability over the length of time before the cigarette is smoked. As in U.S. Pat. No. 3,339,558, the cigarette filter contains in front of the filter a rupturable capsule with a specified amount of Vitamin A and a method of introducing it into the mouth and respiratory tract of the smoker. Prior to lighting up, pressure is applied to the putative capsule, so that the released active materials are dispersed with the filter, thereby the Vitamin A is accessible to the cigarette smoke passing through. The '478 patent further teaches that the stabilized Vitamin A may also be dispersed, impregnated in the tobacco or provided throughout in droplets or beadlets through the employment of gelatin or other colloidal materials, so that the stabilized Vitamin A can be easily entrained by the smoke passing through the filtering elements. Thus, dispersed and random distribution of the small liquid droplets or tiny particulate matter of the Vitamin A preparation is located throughout the tobacco proper or throughout the filtering medium of a filter cigarette. The Vitamin A is surrounded and protected in a method akin to micro-encapsulation.

Irimi and coworkers taught in U.S. Pat. No. 5,060,672, dated Oct. 29, 1991, which is herein incorporated by reference, a highly efficient tobacco smoke filter. They disclosed a composition with mechanically and/or adsorptively filtering materials and one containing a compound having high nucleophilic addivity to formaldehyde so that these are chemically reactive with the aldehydes that are not filtered out. One component contains an enediol structure. The patent points out that the synergistic compositions eliminate the excited formaldehyde radical from the tobacco smoke.

It has been noted that tar in smoke may be reduced by using low tar tobaccos and cigarette filters. Other efforts have been directed in reducing toxic and harmful substances in the tobacco itself or by adding these modifications of filters or adding chemicals to the filters. Caseley taught a method to further reduce aldehydes in tobacco by using non-toxic salts of w-mercapto-alkalene-sulphonates, as well as cysteine and acetylcysteine in U.S. Pat. No. 4,532,947, dated Aug. 6, 1985, which is herein incorporated by reference. These compositions were to be added to cigarette filters or cigarette holders comprising a filter for the purposes of reducing toxic tobacco substances in situ, while smoking cigarettes.

In U.S. Pat. No. 3,972,335, dated Aug. 3, 1976, which is herein incorporated by reference, Tiggelbeck and Mannes disclosed a cigarette filter comprising menthol or other smoke-flavoring agents. They taught the use of impregnating a granular activated carbon with a pore modifying agent, like sucrose, and thereby improve the shelf life and delivery of the smoke flavoring agent. Part of the activated carbon is available for adsorption of the menthol or other flavor.

In U.S. Pat. No. 5,472,002, dated Dec. 5, 1995, which is herein incorporated by reference, discloses a cigarette filter for administering taurine by inhalation. The patent disclosed three methods or devices to administer amino acid to smokers. The disclosure involves a cigarette filter which comprises a filtration material for filtering the smoke from burning tobacco and various means for incorporating taurine therein so that it is introduced into the smoke as it passes through the filter while the cigarette is puffed. Taurine by inhalation has been shown to have preventive and beneficial effects to afflictions of the respiratory tract, including an important mucolytic property. The latter is similar to the action of cysteine, as taught by Puracelli, in U.S. Pat. No. 4,910,222, dated Mar. 20, 1990, also incorporated by reference herein.

A number of investigators have taught cigarette filtering systems to aid in retention of tobacco smoke tars, nicotine and other toxic chemicals. Choen and Luzio in U.S. Pat. No. 5,009,239 dated Apr. 23, 1991, which is herein incorporated by reference, demonstrated a process for improving selective filter retention and pass through properties of cigarette filter elements. They used a polyethylene imine buffered with organic acids such as formic, propionic, lactic, etc. to a pH range of about 8 to 9.5. In this fashion there was retention of aldehyde and nicotine and by-products by the filter from cigarette smoke.

Brown and co-workers in U.S. Pat. No. 5,249,588, dated Oct. 5, 1993, which is incorporated herein by reference, developed a smoking article which comprised tobacco treated with a high level humectant of 4% to 15% by weight. This smoking article comprised a tobacco rod whereby the rod comprised cut expanded tobacco and a paper wrapper, with said tobacco having been loaded with the humectant. Von Borstel and Craig also teach a cigarette filter with a humectant in U.S. Pat. No. 5,501,238 dated Mar. 26, 1996, which also is herein incorporated by reference. They disclosed sodium pyroglutamate as a humectant plus a surfactant such as ethoxylates in order to absorb moisture from the tobacco smoke for wet filtration of the tobacco smoke. They also disclosed that other agents as antioxidants and anticarcinogenic agents that serve to filter or inactivate the toxic component of smoke may be added. The '238 patent disclosed three types of filters to effectively remove tar from smoke: a) conventional cellulose acetate filter, b) cellulose acetate with sodium pyroglutate and c) commercial wet filtration system.

Lee and Harris disclosed in U.S. Pat. No. 4,964,426 dated Oct. 23, 1993, which is herein incorporated by reference, both tobacco smoke filters and a process for their production. The filter element such as cellulose acetate contains at least 1% by weight of microalicular crystals of compounds as sodium carbonate on the surface of the filter element to promote filtration.

Cigarette smoke induces oxidative damage to lipids, DNA and proteins, particularly protein-SH groups for this smoke contains high levels of both free radicals and aldehydes, including acetaldehyde, propanol and acrolein as well as other deleterious molecules. In the oro-pharynx and lung, cigarette smoke also accelerates the production of reactive oxygen species by recruiting locally and activating phagocytic cells in response to the noxious agents. Inhaled smoke first comes into contact with the respiratory tract lining fluids which is the first line of defense with its antioxidants, particularly reduced glutathione, (GSH) and ascorbic acid. Attack by cigarette smoke and free radicals upon plasma proteins may be measured by carbonyl assay and by loss of enzyme activity and SH groups. Reznick et al. [full citation] showed that whole and gas phase cigarette smoke elicit formation of carbonyl groups in human plasma, which is particularly inhibited by GSH. In contrast, exposure of human plasma to gas phase but not to whole cigarette smoke produces oxidative damage to lipids. As such, it is contemplated that the compositions of this invention will contain GSH, ascorbic acid and other synergistic antioxidants, to be in the internal filters of cigarettes or in these external filters of smoking articles or in tobacco itself or in cigarette papers.

SUMMARY OF THE INVENTION

The present invention involves the inclusion of an antioxidant defense system incorporated within a filter to be used with tobacco products or within tobacco or within a wrapper for such tobacco products. The present application utilizes synergistic antioxidants delivered, for example, in tobacco filters such as those for cigarettes or external filters to prevent and ameliorate free radical damage induced by smoking to the oro-pharynx, respiratory tract and lungs. The composition is supplied by inhalation through various state of the art filters. The invention in its broadest terms comprises glutathione in its reduced form and a co-ingredient for regenerating the reduced form of the glutathione, the later ingredient comprising selenium as seleno amino acid such as selenomethionine or selenocysteine. As further optional ingredients, it is contemplated that the composition include ascorbic acid and/or one of its derivatives, a sulfur containing amino acid such as L-cysteine, L-taurine and/or L-methionine alpha tocopherol, vitamins A and E and zinc salts.

In a most preferred aspect of the present invention, the aforementioned pharmaceutically active antioxidant system included within a filter comprises L-ascorbic acid, about 1.0 mg., reduced L-glutathione, 2.0 mcgm selenium as selenomethionine and about 0.5 mg. of L-cysteine. The composition may also have about 2.0 I.U. of D, L-alpha tocopherol acetate and about 2.0 I.U. of Vitamin A. These are preferred amounts in the filter of each cigarette or in the capsules next to the filter with these ingredients encapsulated in liposomes.

DETAILED DESCRIPTION OF THE INVENTION

Without being bound to any particular theory, it is noted that reduced glutathione is employed in protecting cells against oxidative stress by itself being oxidized. Thus, L-glutathione must act in combination with other enzyme systems in order to be reduced so that it may renew its role as a free radical scavenger. GSH functions also coordinately with the enzyme glutathione peroxidase which requires selenium as a cofactor to exert its biologic antioxidant function. Selenium compounds have been shown to scavenge oxygen-centered radicals in vivo with reduced glutathione through glutathione peroxidase. It is believed that selenium-GSH peroxidase catalyzes toxic hydrogen peroxidase in the presence of reduced glutathione. This reaction reduces glutathione to oxidized glutathione GSSG. In turn, the GSSG is reduced back to GSH by the enzyme glutathione reductase thereby maintaining abundant cellular GSH to scavenge free radicals anew.

Further, glutathione and selenium act synergistically in vivo as they are both constituents of the same enzymatic system. GSH serves as a specific donor substrate while selenium, provided from alimentary sources or locally from topically applied preparations of selenium, or selenoaminio acids, provides the prosthetic group of GSH peroxidase. The glutathione and selenium antioxidant functions are intrinsically related since by keeping a peroxidase in action, the GSH and selenium, contribute to the removal of the dismutation product of free oxygen radicals, namely, hydrogen peroxide. In a broad sense, GSH and selenium modulate free radical chains initiated or sustained by hydroperoxides. Selenium is used in the present invention for its role as an antioxidant as well as its anticarcinogenic and antimutagenic properties.

The aforementioned compositions may be particularly useful in the prevention and treatment of tobacco smoke or other gaseous or particulate matter exposure. They represent a delicate balance of ingredients which serve not only to reduce the number of free radicals but also to inhibit the metabolic oxidation in tissues. The more preferred formulations in accordance with the present invention also enhance the performance of the composition by recycling certain antioxidant ingredients in the formulation after these are absorbed.

In the preferred embodiment of this invention, the synergistic antioxidant complex is a dispersion of active materials throughout the filtering medium of a tobacco filter, although, as noted previously, the complex can also be incorporated in the tobacco itself or in the paper wrapper. The antioxidant complex would be dispersed in the filter as a powder, as a stable solution, or as an aqueous emulsion, which may include the micro-encapsulation of these actives, such as in liposomes. The actives may also be in tiny droplets so that when the smoke produced by the burning tobacco passes through the filter, the smoke will pick up or entrain the powdered complex or the tiny droplets containing the putative antioxidant ingredients. Thus the smoke with the actives is inhaled by the smoker as the smoke enters the oral cavity and then inhaled into the respiratory tract and lungs of the individual. The antioxidants will then be able to neutralize and scavenge the free radicals both in the tobacco smoke itself and those generated by the deleterious tobacco smoke in the oral cavity and respiratory tract, and thereby the complex will exert its beneficial effects locally in the mucosa and tissues of the smoker.

As noted above as an alternative in both filtered and unfiltered cigarettes, it is contemplated that the present antioxidant complex be dispersed throughout the tobacco charge of the product. Although these can be localized near the distal end of the filter tip or the proximal opening of the unfiltered tobacco product, the antioxidant complex may also be uniformly and evenly distributed throughout the entire product. Thus, particularly by employing micro-encapsulation techniques such as oral liposomes, these active ingredients may be administered in the filtering medium of a filtered cigarette and within the tobacco charge of these, or of non-filtered cigarettes and cigars.

In order to protect the active ingredients of this invention, various encapsulating or chemically protective techniques are available such as are well known in the art. The actives may be incorporated in micro-encapsulation vehicles such as liposomes, glycospheres and nonospheres. Such vehicles for oral use as are well known to the cosmeceutical industry. Liposomes are lecithin spheres that form an oil protective membrane around the active ingredient composition of this invention. The liposome entrapped active ingredients travel from the tobacco product and are delivered to the oral cavity where locally they exert both their preventative and therapeutic functions to neutralize the various free radical species. In addition, the antioxidants may also be absorbed as usual by the buccal mucosa for systemic use. It is noted that Unger and co-workers have taught therapeutic drug delivery systems comprising gas filled liposomes which encapsulate the active preparation in U.S. Pat. No. 5,580,573 dated Dec. 3, 1996 which is herein incorporated by reference. Earlier, Chakrabarti and Associates disclosed preparations comprising a lipid and a modified peptide using liposomes as delivery vehicles. See U.S. Pat. No. 5,380,531 dated Jan. 10, 1995 which is also herein incorporated by reference. Knight and co-workers in U.S. Pat. No. 5,049,388 dated Sep. 17, 1991 which is also herein incorporated by reference, disclosed small particle aqueous aerosol droplets containing liposomes. The patentees taught the inclusion of a drug or medication interacted within the liposome membrane so that when the latter ruptures the active ingredient is not lost from the liposome. The inventors teach various method of preparation of the aerosol particles containing the liposome. Interacted liposome-drug combination particles are used in small particle aerosol treatments.

Liposome particles as contemplated herein have a diameter of less than five microns and can easily be prepared in uniform size with the actives for dispersion in filtering material of cigarette filter or in the rupturable aqueous capsule which contains the liposome encapsulating the antioxidants. In each case, the active compost in the liposomes would be inhaled by the smoker with each puff, thereby neutralizing free radicals in the oro-pharynx and respiratory tract and lungs generated by the tobacco smoke.

Alternatives to placing the antioxidants of this invention in the filter, tobacco or in encapsulations in front of the filter is to affix these in a treated cigarette paper. This would reduce particularly the free radicals in the sidestream smoke which are particularly injurious to those exposed to secondary smoke as well as to the primary smoker in both main stream and side stream smoke. Chad and co-workers disclosed in U.S. Pat. No. 5,540,242, dated Jul. 30, 1996, which is herein incorporated by reference, a method for reducing side-stream smoke by incorporating additives to the cigarette smoke. Their paper includes an alginate as a film forming agent in combination with a burn additive like alkali metal salts as potassium succinate, citrate or acetate to form a coating that will reduce sidestream smoke. The synergistic group of antioxidants of this invention may be incorporated in the cigarette paper to not only reduce sidestream smoke, but also to neutralize free radicals in inhaled tobacco smoke. The paper so treated will not produce an off-taste, modify ash appearance, or reduce the cigarette's puff count. The filter, may as well contain powdered antioxidant complex to be inhaled by the smoker and may or may not contain a menthol flavor, as is known in the art.

Treating tobacco to reduce or inhibit toxic chemicals in tobacco smoke have been reported. For example, Wadell and Colleagues disclosed in U.S. Pat. No. 4,967,772, dated Nov. 6, 1990, a smoking article whereby the tobacco and an alcohol are held in a container. This patent is herein incorporated by reference as it teaches that the alcohol is akin to a cyclohexanol, whose vapor is inhaled in the tobacco smoke stream. It is said to inhibit the selective localization of toxic tobacco nitrosamnes and its derivatives or methobolites in the tissues of the smoker without untold alcohol effects from this vapor in the smoke. Wadell in U.S. Pat. No. 4,966,169 dated Oct. 30, 1990, also herein incorporated by reference, teaches redried cut rag tobacco which is directly sprayed with an alcohol. The patentee notes that this process reduces tobacco health risks as the concomitantly smoked alcohol is heat released and in the bronchial tissues is able to block the localization of the putative nitrosamines.

In a preferred embodiment of this invention, the active ingredients comprising a group of synergistic antioxidants are to be employed in the following dosages in the filter of each cigarette. It must be recognized that to express the amount per pack of cigarettes, each value will be multiplied by 20, the usual numbers of cigarettes sold in one pack, with 10 packs in one carton. The ranges of each ingredient are expressed whether each is dispersed in the filtering material of each cigarette, as a powder or a gel or encapsulated in beads or admixed with a super absorber such as any acrylamide co-polymers or as polyvinyl alcohol engrafted with maleic anhydride. In the latter case, the actives are first solubilized in glycerin and then mixed with the superabsorber in proportions ranging from at least 1 to 1,000 parts of actives to at least 1 to 10,000 parts of the super-absorber depending on its capacity to hold an aqueous glycerin based active complex.

In another preferred embodiment of this invention, the active synergistic anti-oxidants are first micro-encapsulated in such protective phospholipid vehicles as oral liposomes or by other state of the art micro-encapsulation techniques, as already noted and which are well known in this industry for protection of oral drugs, vitamins, amino acids, peptides, etc.

The active ingredients are as follows:

1. L-glutathione in an amount between at least 0.01 mg. to 20 mg., preferably from 0.10 to 10 mg, most preferably from 1.0 mg to 5.0 mg per cigarette.
2. L-selenomethionine or I-selenocysteine at a concentration to yield at least 0.01 mcgm to 10 mcgm of selenium, preferably 1.0 to 2.5 mcg selenium per cigarette.

Optional Ingredients

3. L-cysteine and/or its ester, n-acetyl-l-cysteine in a range of 0.1 mg to 10.0 mgs., preferably from 0.5 mg to 5.0 mgm and most preferably from 1.0 mgs to 2.5 mgm, per cigarette.

4. Vitamin C as ascorbic acid or as an ascorbyl palmitate or other ascorbic acid esters alone or microencapsulated such as in liposomes from 0.1 mg to 60.0 mg, preferably from 0.5 mg to 30.0 mgm, most preferably from 1.0 mgm to 3.0 mgm per cigarette.
5. Vitamin E as a powder for dispersion as tocopherol acetate or tocopherol succinate or other esters from 0.0 I.U. to 10.0 I.U., preferably from 1.0 I.U. to 5.0 I.U. per cigarette. Vitamin E may also be used in liposomes at approximately the same dosages.
6. Vitamin A activity as beta-carotene or a retinyl palmitate or other vitamin A stabilized esters in an amount between approximately 1.0 I.U. to 500 I.U., preferably from 10.0 I.U. to 250 I.U., most preferably from 25.0 to 125 I.U. per cigarette. Vitamin A compositions may also be administered by being micro-encapsulated, such as in liposomes.
7. As an optional ingredient, the compositions of the present invention may include a zinc salt, preferably a zinc acetate or zinc gluconate in an amount from approximately 0.1 to 15 mg., preferably from 90.5 to 7.5 mg., most preferably from 0.75 mg. To 1.5 mg per cigarette.
8. As further optional ingredients the amino acids methionine and/or taurine, as already noted, may be included each in concentrations of at least approximately 0.5 mg. to 20 mg., preferably from 1.0 mg. to 10 mg. per cigarette.

In each instance, the above and below-noted level of ingredients are based upon a single cigarette filter whether contained within the filter as being absorbed upon the filter material or as a rupturable capsule or as a separate stand alone filter for use with cigars, pipes and unfiltered cigarettes. When used in cigars or as additives to pipe tobacco, the gross amounts of the above-noted ingredients can be adjusted in proportion to the amount of tobacco as compared to the amount of tobacco contained in the typical cigarette.

In the most preferred embodiment of this invention the same ingredients can be provided in an aqueous solution as a rupturable capsulte with the following composition:

1. L-glutathione, at least 0.01% to 2.0% most preferably from 0.05 to 1.0% by weight.
2. L-selenomethione from at least 0.01 to 1.0% most preferably from 0.05 to 0.1% by weight.
3. L-cysteine and/or its ester N-acetyl-L-cysteine from at least 0.01% to 2%, most preferably from 0.05% to 0.5% by weight for each amino acid.
4. Ascorbic acid or its esters at 0.1% to 2.0%, most preferably from 0.5% to 1.0% by weight.
5. Vitamin E or one of its esters at 0.05 to 1.0%, most preferably from 0.1% to 0.25% by weight.
6. Vitamin A or one its esters at 0.1% to 10%, most preferably from 0.5% to 1% by weight.
7. Amino acids, taurine and/or methionine from 0.05% to 1.0%, most preferably from 0.1% to 0.5%, by weight of each amino acid.

In one embodiment of this invention, optional ingredients, particularly exogenous antioxidants may be added to the synergistic complex in either the filter or a receptacle capsule. These free radical scavengers employed as antioxidants can be used in each cigarette or its filter:

Japanese green tea (catechins) approximately 1.0 mcg
Pycnogenol approximately 0.05 mg.
Superoxide Dismutase approximately 0.01 mg.
Co-enzyme Q approximately 0.25 mcgm.
N-Acetyl-L-Carnitine approximately 0.01 mgm.

Other optional ingredients can be used in the tobacco or in the filter which may include those ingredients which are known to bind, or chemically alter noxious molecules, such as aldehydes found in tobacco smoke. The putative antioxidants of this invention are used to neutralize the free radicals found in tobacco as well as those generated by tobacco smoke in the oral cavity, as the antioxidants are inhaled from the filter in the smoke with each puff.

We claim:

1. A composition for inclusion within a cigarette, cigar or pipe tobacco for reducing free radical damage to the oropharyngeal cavity, respiratory tract and lungs from tobacco smoke, said composition comprising L-glutathione and a source of selenium selected from the group consisting of L-selenomethionine and L-selenocysteine.

2. The composition of claim 1 further comprising vitamin C as a member selected from the group consisting of ascorbyl palmitate and ascorbic acid esters.

3. The composition of claim 1 further comprising a member selected from the group consisting of L-cysteine and N-acetyl-l-cysteine.

4. The composition of claim 1 further comprising vitamin E as a member selected from the group consisting of tocopherol acetate and tocopherol succinate.

5. The composition of claim 1 further comprising vitamin A.

6. The composition of claim 1 further comprising a zinc salt.

7. The composition of claim 1 further comprising methionine and taurine.

8. The composition of claim 1 wherein said composition is included within a cigarette wherein said L-glutathione is contained with an amount between at least 0.01 to 20 mgs and the source of selenium is contained in an amount between approximately 0.01 to 10 mcgm.

9. The composition of claim 2 for inclusion within a cigarette wherein said vitamin C is contained in an amount between approximately 0.1 mgs to 60 mgs.

10. The composition of claim 3 for inclusion within a cigarette wherein said L-cysteine or its ester N-acetyl-l-cysteine is contained in an amount between approximately 0.1 mgs to 10 mgs.

11. The composition of claim 4 for inclusion within a cigarette wherein said vitamin E is contained in an amount between approximately 0.01 I.U. to 10.0 I.U.

12. The composition of claim 5 for inclusion within a cigarette wherein said vitamin A is contained in an amount between 1.0 I.U. to 500 I.U.

13. The composition of claim 6 for inclusion within a cigarette wherein said zinc salt is comprised as a member selected from the group consisting of zinc acetate and zinc glutonate in an amount from approximately 0.1 to 15 mgs.

14. The composition of claim 7 for inclusion within a cigarette wherein said methionine and taurine are included in amounts between approximately 0.5 mgs to 20 mgs.

15. A cigarette comprising a paper wrapper surrounding a charge of tobacco, said cigarette further comprising a composition for reducing free radical damage to the oropharyngeal cavity, respiratory tract and lungs from tobacco smoke generated by said cigarette, said composition comprising L-glutathione and a source of selenium selected from the group consisting of L-selenomethionine and L-selenocysteine.

16. The cigarette of claim 15 further comprising vitamin C as a member selected from the group consisting of ascorbyl palmitate and ascorbic acid esters.

17. The cigarette of claim 15 further comprising a member selected from the group consisting of L-cysteine and N-acetyl-l-cysteine.

18. The cigarette of claim 15 further comprising vitamin E as a member selected from the group consisting of tocopherol acetate and tocopherol succinate.

19. The cigarette of claim 15 further comprising vitamin A.

20. The cigarette of claim 15 further comprising a zinc salt.

21. The cigarette of claim 15 further comprising methionine and taurine.

22. The cigarette of claim 15 wherein said composition of L-glutathione is contained with an amount between at least 0.01 to 20 mgs and the source of selenium is contained in an amount between approximately 0.01 to 10 mcgm.

23. The cigarette of claim 16 wherein said vitamin C is contained in an amount between approximately 0.1 mgs to 60 mgs.

24. The cigarette of claim 17 for inclusion within a cigarette wherein said L-cysteine or its ester N-acetyl-l-cysteine is contained in an amount between approximately 0.1 mgs to 10 mgs.

25. The cigarette of claim 18 for inclusion within a cigarette wherein said vitamin E is contained in an amount between approximately 0.01 I.U. to 10.0 I.U.

26. The cigarette of claim 19 for inclusion within a cigarette wherein said vitamin A is contained in an amount between 1.0 I.U. to 500 I.U.

27. The cigarette of claim 20 for inclusion within a cigarette wherein said zinc salt is comprised as a member selected from the group consisting of zinc acetate and zinc glutonate in an amount from approximately 0.1 to 15 mgs.

28. The cigarette of claim 21 for inclusion within a cigarette wherein said methionine and taurine are included in amounts between approximately 0.5 mgs to 20 mgs.

29. A filter for filtering smoke generated by a tobacco product, said filter comprising a filtration material for filtering the smoke from burning tobacco which passes through said filtration material and an antioxidant composition which is dispensed into said smoke as it passes through said filtration material, said composition comprising L-glutathione and a source of selenium selected from the group consisting of L-selenomethionine and L-selenocysteine.

30. The filter of claim 29 further comprising vitamin C as a member selected from the group consisting of ascorbyl palmitate and ascorbic acid esters.

31. The filter of claim 29 further comprising a member selected from the group consisting of L-cysteine and N-acetyl-l-cysteine.

32. The filter of claim 29 further comprising vitamin E as a member selected from the group consisting of tocopherol acetate and tocopherol succinate.

33. The filter of claim 29 further comprising vitamin A.

34. The filter of claim 29 further comprising a zinc salt.

35. The filter of claim 29 further comprising methionine and taurine.

36. The filter of claim 29 wherein said composition of L-glutathione is contained with an amount between at least 0.01 to 20 mgs and the source of selenium is contained in an amount between approximately 0.01 to 10 mcgm.

37. The filter of claim 30 wherein said vitamin C is contained in an amount between approximately 0.1 mgs to 60 mgs.

38. The filter of claim 31 for inclusion within a cigarette wherein said L-cysteine or its ester N-acetyl-l-cysteine is contained in an amount between approximately 0.1 mgs to 10 mgs.

39. The filter of claim 32 for inclusion within a cigarette wherein said vitamin E is contained in an amount between approximately 0.01 I.U. to 10.0 I.U.

40. The filter of claim 33 for inclusion within a cigarette wherein said vitamin A is contained in an amount between 1.0 I.U. to 500 I.U.

41. The filter of claim 34 for inclusion within a cigarette wherein said zinc salt is comprised as a member selected from the group consisting of zinc acetate and zinc glutonate in an amount from approximately 0.1 to 15 mgs.

42. The filter of claim 35 for inclusion within a cigarette wherein said methionine and taurine are included in amounts between approximately 0.5 mgs to 20 mgs.

43. The filter of claim 29 wherein said antioxidant composition is encapsulated as a member selected from the group consisting of liposomes, glycospheres and nonospheres.

44. The filter of claim 29 wherein said composition for reducing free radical damage is incorporated within said filter as a powder.

45. The filter of claim 29 wherein said composition for reducing free radical damage is incorporated within said filter as a gel.

46. The filter of claim 29 wherein said composition is mixed with a super absorber selected from the group consisting of acrylamide co-polymers and polyvinyl alcohol and grafted with maleic anhydride.

47. The filter of claim 29 wherein said composition for reducing free radical damage is contained within an aqueous solution in the form of a rupturable capsule.

* * * * *